United States Patent
Fountain

(10) Patent No.: US 6,913,150 B1
(45) Date of Patent: Jul. 5, 2005

(54) MEDICAL TOOL CARRIER

(76) Inventor: Cynthia Fountain, 10301 Ridge Park Dr., Anchorage, AK (US) 99507

( * ) Notice: Subject to any disclaimer, the term of this patent is extended or adjusted under 35 U.S.C. 154(b) by 295 days.

(21) Appl. No.: 10/300,379

(22) Filed: Nov. 20, 2002

(51) Int. Cl.⁷ .......................... B65D 71/00; B65D 85/46
(52) U.S. Cl. ...................................... 206/570; 206/223
(58) Field of Search ................................ 206/570, 571, 206/572, 576, 320, 216, 223, 438, 806; 5/503.1, 5/658, 308; 383/22, 23, 24, 38

(56) References Cited

U.S. PATENT DOCUMENTS

| | | | | |
|---|---|---|---|---|
| 3,301,295 A | * | 1/1967 | Fitch | 190/100 |
| 4,796,790 A | * | 1/1989 | Hamilton | 224/675 |
| 5,108,000 A | * | 4/1992 | Stoll et al. | 220/23.4 |
| 5,143,243 A | * | 9/1992 | Colling | 220/694 |
| 5,447,237 A | * | 9/1995 | Carter et al. | 206/570 |
| 5,876,371 A | * | 3/1999 | Yokoyama et al. | 604/80 |
| 6,012,585 A | * | 1/2000 | Parker | 206/570 |
| 2003/0160076 A1 | * | 8/2003 | Lofaro | 224/275 |
| 2004/0187212 A1 | * | 9/2004 | Pacella | 5/503.1 |

* cited by examiner

*Primary Examiner*—Derris H. Banks
*Assistant Examiner*—Faye Francis
(74) *Attorney, Agent, or Firm*—Michael J. Tavella

(57) ABSTRACT

A storage box that can be attached to a patient's bed rail. The box has a number of slots, cavities, and hooks that can be used to hold a wide range of medical equipment. Unlike the devices mentioned above, this device allows practitioners to hold items larger than tubes and more specific than medicine jars in one container. Moreover, the container has shaped cavities that make sorting of the equipment easy and fast. Finally, the shaped cavities also ensure that the proper equipment is used and placed in the proper location to reduce the chance of error in the administration of various treatments.

14 Claims, 5 Drawing Sheets

MEDICAL TOOL CARRIER

CROSS REFERENCE TO RELATED APPLICATIONS

Not Applicable

STATEMENT REGARDING FEDERALLY SPONSORED RESEARCH AND DEVELOPMENT

Not Applicable

BACKGROUND OF THE INVENTION

1. Field of the Invention

This invention relates to medical tool carriers and particularly to medical tool carriers attached to patient's bedsides.

2. Description of the Prior Art

The medical field has become a user of many technologies. These technologies use a vast array of equipment. Devices must be brought into a patient's room and set up for use in a convenient and efficient way so that nurses and technicians can readily make use of the equipment as needed. To that end, several devices have been developed to hold various pieces of equipment in hospital rooms. Examples of these devices are found in the following U.S. Patents: U.S. Pat. No. 6,012,585, which describes a caddie for sickroom use for storing medicine containers, thermometers, cups and the like that has a base, a back panel which supports the rear edge of a solid lower shelf, a second, upper shelf having multiple apertures formed therein which are preferably of annular cross-section having diameters slightly greater than the diameter of the standard size medication containers, but less than the diameter of the threaded caps which are placed upon the medicament containers. U.S. Pat. No. 5,651,152 describes a removably attachable storage organizer that hangs on the upper most surface of a hospital bed rail. Inner and outer facing panels have attached to them a plurality of pockets capable of storing a variety of personal items that a patient may have with them during a stay at the hospital. For example, a slit front surface is used for the dispensing of facial tissue and a framed front surface can be used for inserting a photograph and the like. U.S. Pat. No. 5,334,186 teaches a medical implement and tubing organizer that allows medical implements to be held in a convenient location proximate to a patient and also allows the medical tubes to be organized and ordered according to size. Finally, U.S. Pat. No. 4,795,441 describes an improved medication administration system includes a series of one way valves disposed closely adjacent and in direct fluid communication with an auxiliary IV line leading to a patient. A number of syringes filled with various selected medications are each secured in a tray against axial and lateral movement by depressing them into correspondingly dimensioned longitudinal grooves. The flanges of the syringes abut a lip of the tray to further restrict axial movement. The nozzles of the syringes are connected to the inlets of the valves so that medication can be administered intravenously by simply depressing the appropriate syringe plunger.

While all of these devices are useful, they are made for either broad general purposes or extremely narrow and limited purposes (the first two cover almost anything that can be stored in a hospital room while the latter two deal exclusively with IV lines and tubes).

BRIEF DESCRIPTION OF THE INVENTION

The instant invention overcomes the limitations of the prior art described above. It is a storage box that can be attached to a patient's bed rail. The box has a number of slots, cavities, and hooks that can be used to hold a wide range of medical equipment. Unlike the devices mentioned above, this device allows practitioners to hold items larger than tubes and more specific than medicine jars in one container. Moreover, the container has shaped cavities that make sorting of the equipment easy and fast. The shaped cavities also ensure that the proper equipment is used and placed in the proper location to reduce the chance of error in the administration of various treatments. Moreover, this organization of equipment decreases the chance of contamination. For example, oxygen tubes will not fall on the floor. It eliminates the possibility of spillage from the nasogastric suction tubing. Finally, it is safer in that the unit has a place for holding sharps, which reduces the possibility of them being left on a bed or at the bedside.

DETAILED DESCRIPTION OF THE INVENTION

Figure 1:
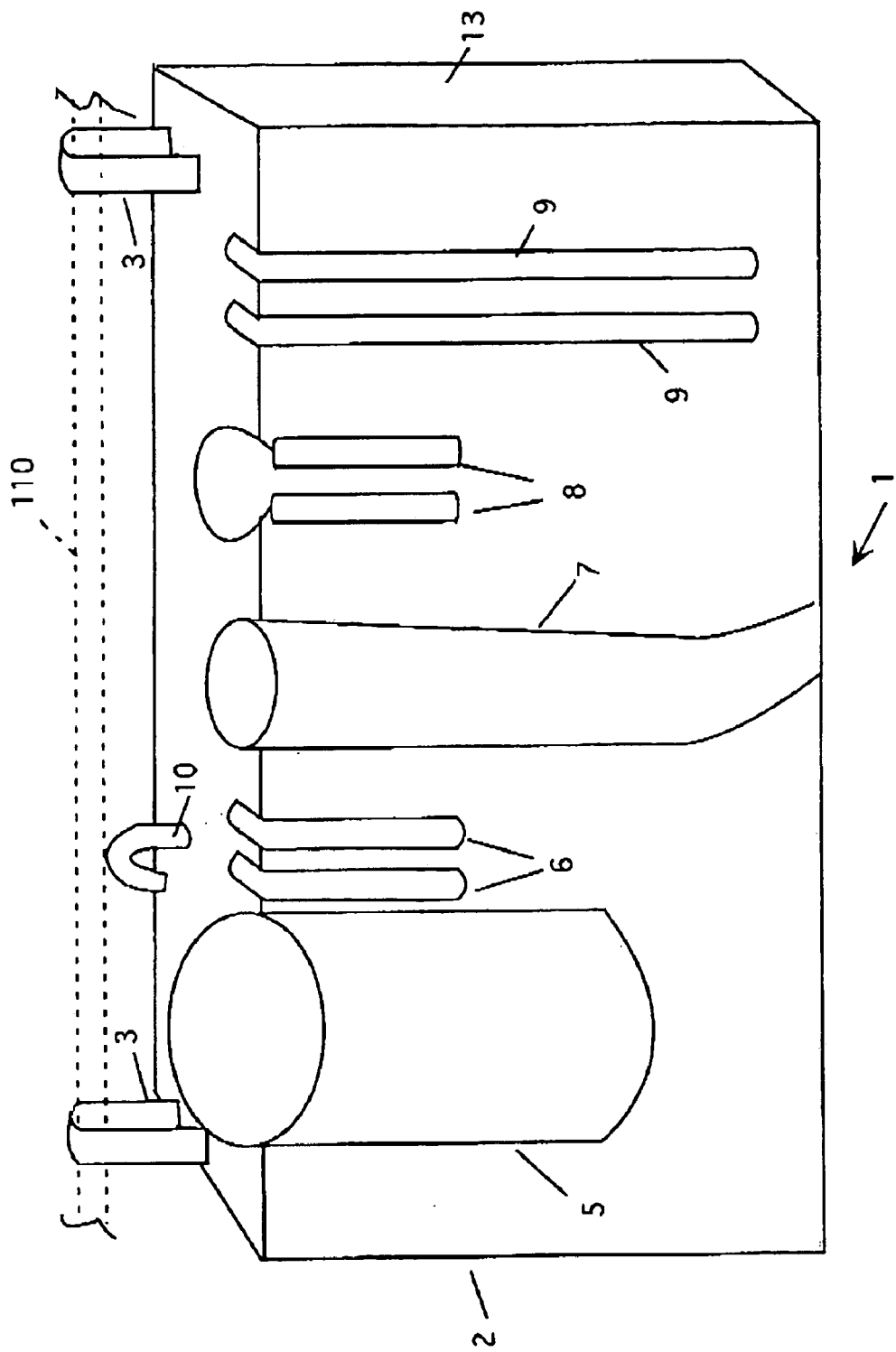
FIG. 1 is a front view of one embodiment of the invention.

Referring now to FIG. 1, the first embodiment of the invention is shown. In this view the equipment carrier 1 is in the basic form. It consists of a formed housing 2 that has two support straps 3 attached to the top as shown. The support straps can have hook and loop type fasteners, clips or buckles, all of which are common to the art. The straps 3 are used to hang the carrier 1 from a side rail 110 of a patient's bed.

The equipment carrier 1 has a number of formed cavities. The first cavity 5 is a cylindrical (or square) opening that is used to hold lab tubes, syringes and caps, and other miscellaneous items. Next to the first cavity is a pair of formed slots 6. These slots are used to hold IV tubes. Next to them, is a conical cavity 7. This cavity has a curved base and is used to hold an oral suction instrument. Next to that is a cavity 8 used for Keofeed tubing and cap. Next to that is a pair of slots 9 used to hold nasogastric suction tubing. Finally, on the top of the housing 2 is a hook 10 used to hold O₂ tubing.

Figure 2:
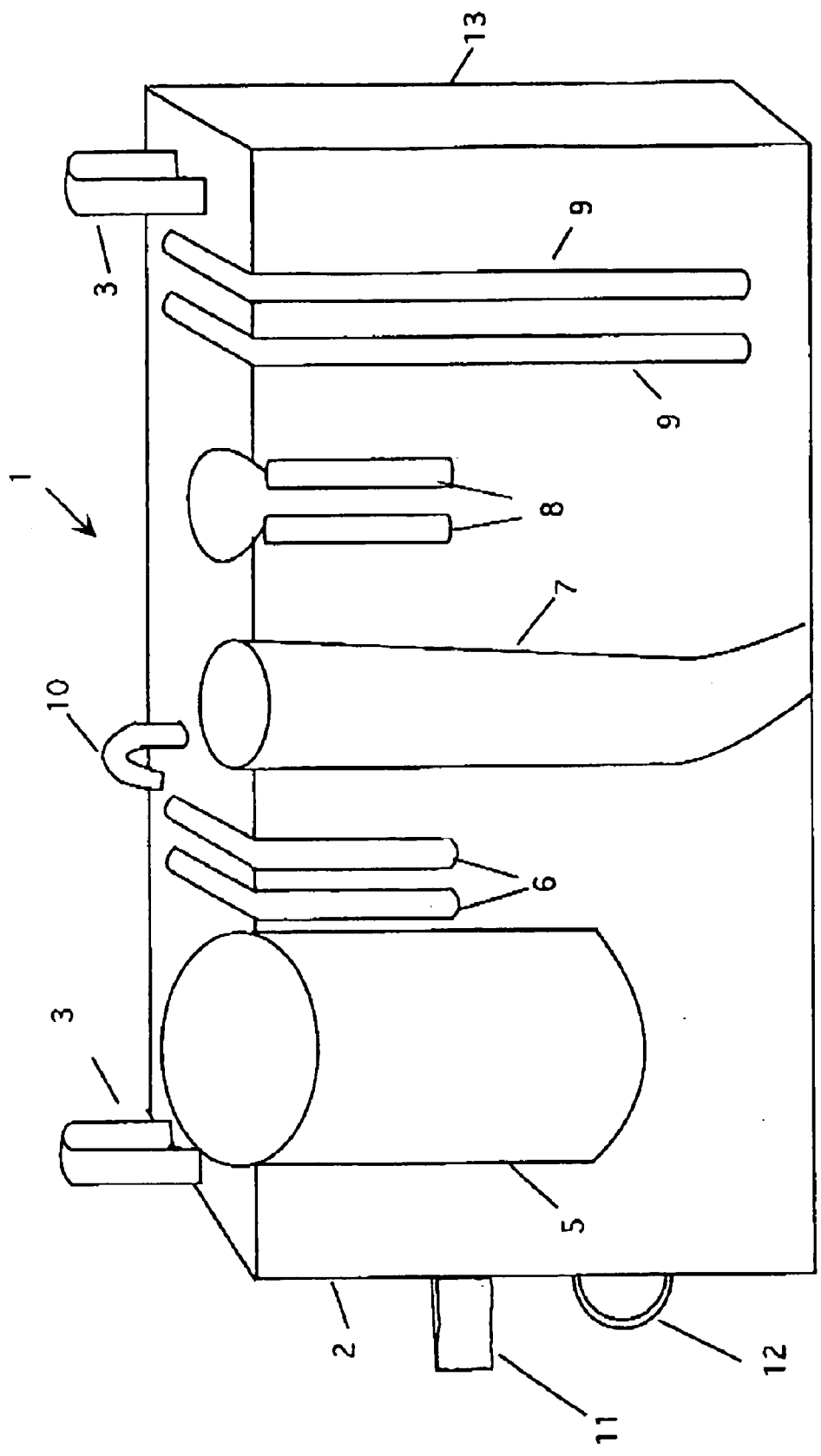
FIG. 2 is a front view of a second embodiment of the invention.

FIG. 2 shows a second embodiment. In this view, the basic elements remain as described above. In this embodiment, an additional strap 11 is placed on the side. Also, a ring 12 that can hold either a urinal or a foley bag. All other aspects of the device are the same as before.

Figure 3:
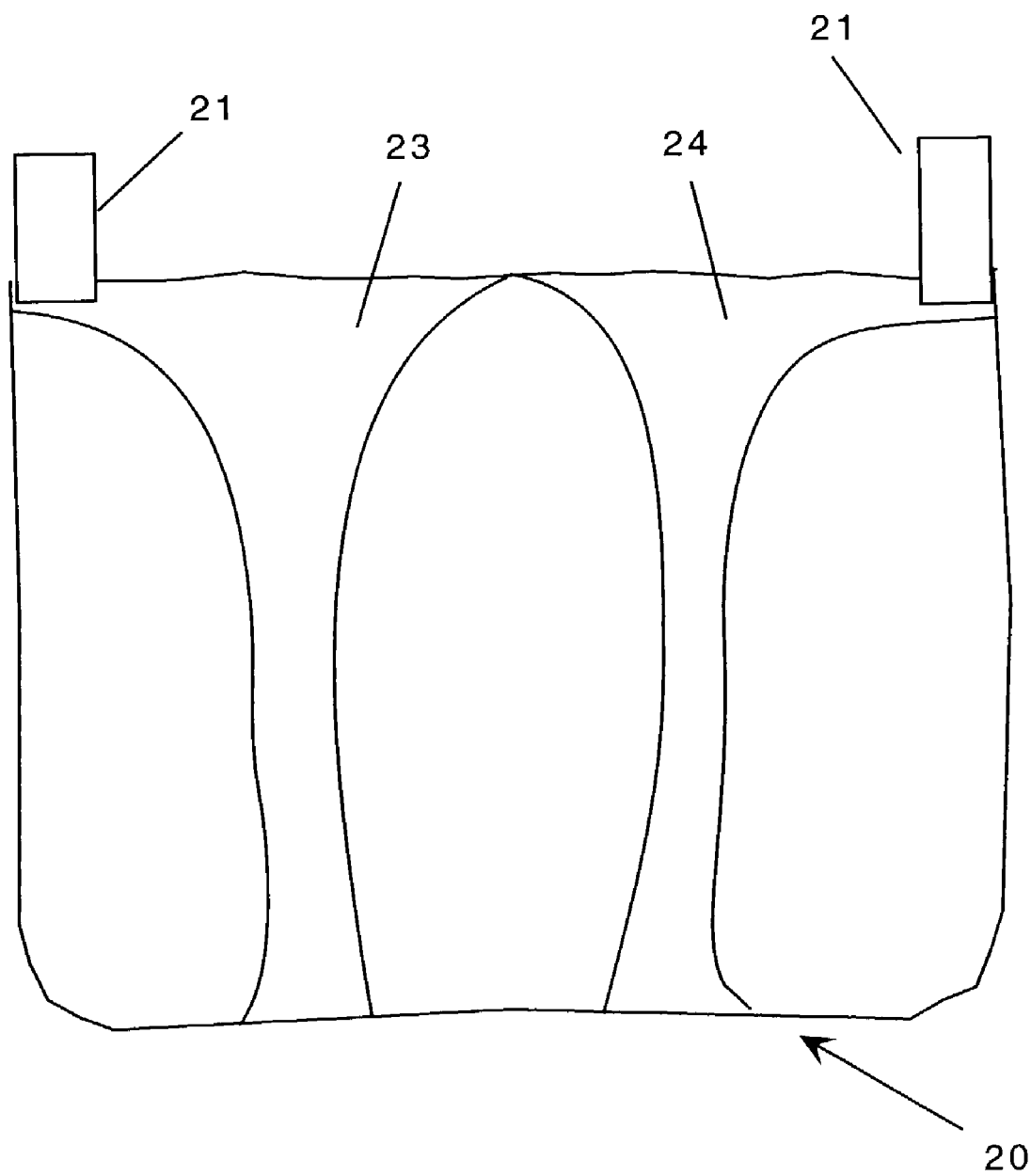
FIG. 3 is a front view of an optional storage pouch piece.

FIG. 3 shows an optional storage pouch 20 that can be used with either embodiment. The storage pouch 20 is placed on the side 13 of the housing 2. Two straps 21 are used to attach the storage pouch to the housing. In the preferred embodiment, the straps 21 are lengths of hook and loop type fastener that attach to mating hook and loop type fasteners 22 (see FIG. 4) that are placed on the top of the housing as shown.

Figure 4:
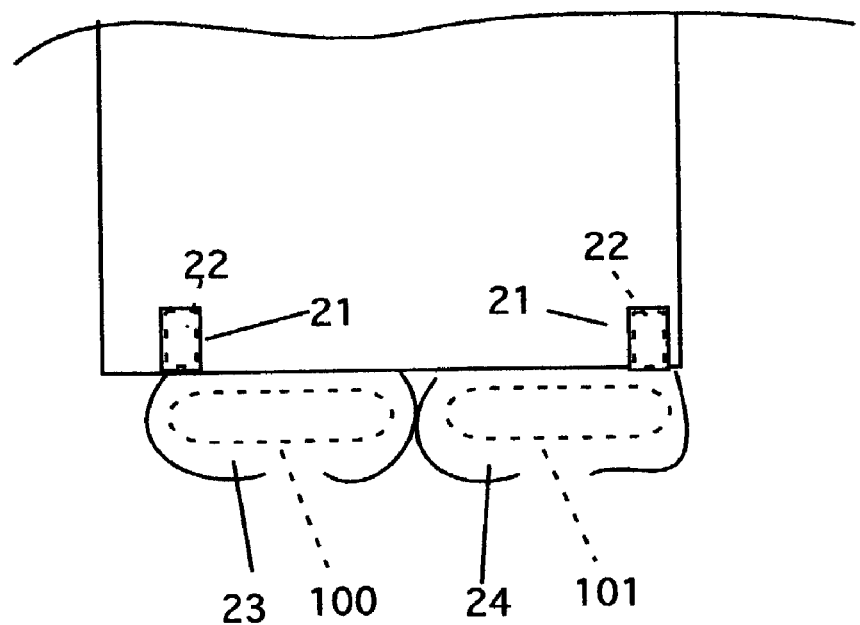
FIG. 4 is a top view of the optional storage pouch piece.

The storage pouch has two pockets 23 and 24 is designed to hold a nurse call control 100 in one of the pockets and a portable phone 101 or TV remote control in the other. Of course these pockets can be used for other items as well. FIG. 4 shows a top view of the storage pouch 20 loaded with a nurse call control 100 in pocket 23 and a portable phone 101 in pocket 24. FIG. 4 also shows the straps 21 in place on the housing and the matching straps 22 in dashed line.

Figure 5:
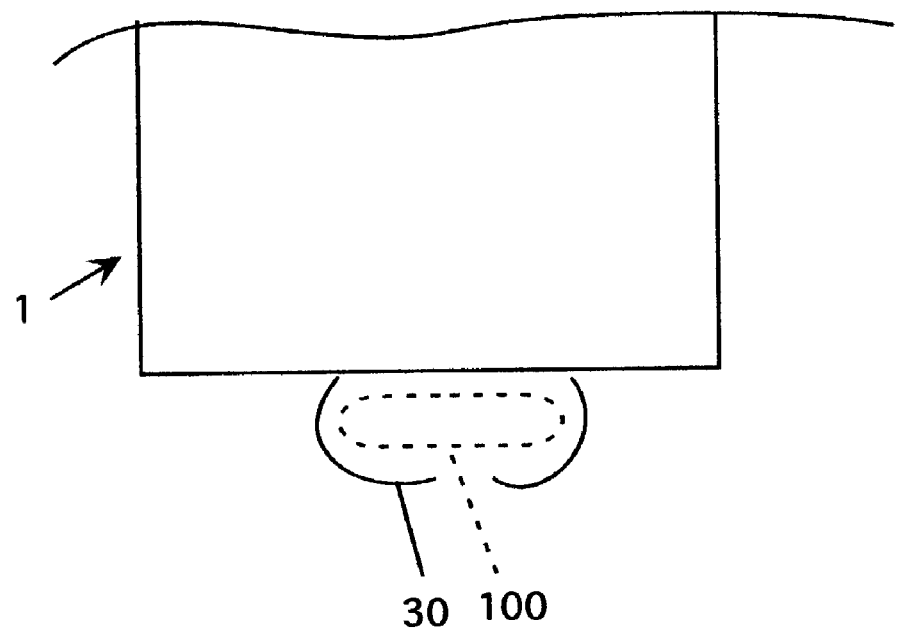
FIG. 5 is a top view of an alternative optional storage pouch piece.
Figure 6:
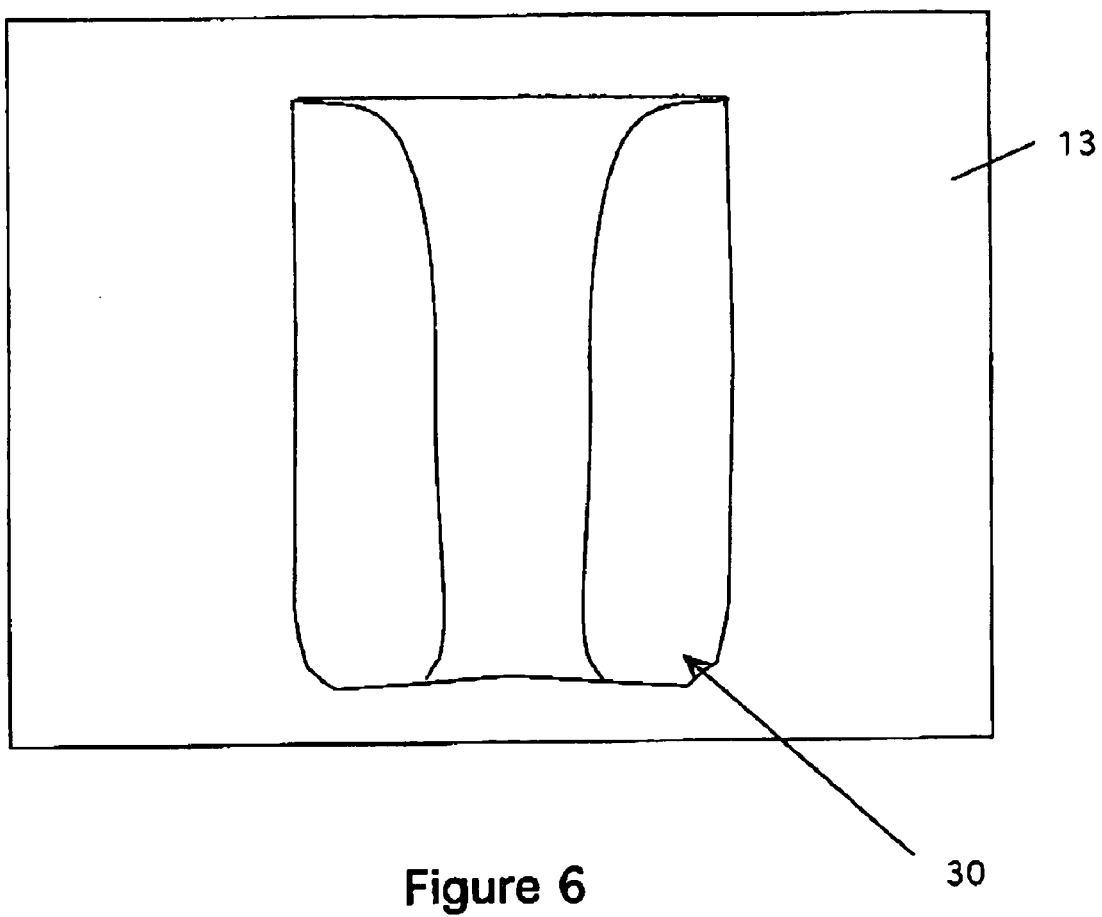
FIG. 6 is a front view of an alternative optional storage pouch piece.

FIGS. 5 and 6 show an alternative optional storage pouch. In this embodiment, a single storage pouch 30 is shown. The storage pouch is permanently attached to the housing. As shown in FIG. 5, there are no straps to attach the storage pouch to the housing. FIG. 6 shows a front view of the storage pouch 30 installed on the housing.

Although FIGS. 3 and 4 show a removable storage pouch and FIGS. 5 and 6 show a fixed storage pouch, either embodiment of optional storage pouch, single or double, can be permanently attached or removable with straps. Moreover, the optional storage pouch need not be limited to a single or double storage pouch.

In the preferred embodiment, the housing 2 is made of plastic and has rounded corners to help prevent injury. The various cavities can be molded into the housing when it is formed. The placement of the cavities can be also changed as desired. However, the placement of the various tubing slots is designed to prevent contamination of sterile equipment by separating the IV tubing from the nasogastric suction tubing. Moreover, not all of the pieces of equipment may be used at any given time with any given patient. The device can be used in any situation and, because it has spaces for all of the items of equipment, any additional equipment can be added easily to the unit once it is in place.

Thus, the tool carrier eliminates the need to lay these items on a patient's bed or to temporarily secure them to a bed rail in a jury rig fashion. Nor is it necessary to secure items to a flat tray or other general-purpose carrier. Here, There is a place for all of the needed equipment when it is needed. Once installed, medical personal can focus on serving the patient with the proper equipment without having to concern themselves with supports or other needed apparatus for the equipment.

The present disclosure should not be construed in any limited sense other than that limited by the scope of the claims having regard to the teachings herein and the prior art being apparent with the preferred form of the invention disclosed herein and which reveals details of structure of a preferred form necessary for a better understanding of the invention and may be subject to change by skilled persons within the scope of the invention without departing from the concept thereof.

I claim:

1. An equipment carrier for use in hospitals for attachment to a bed rail comprising:
    a) a generally rectangular carrier box, said carrier box having means for removably attaching said carrier box to said bed rail, said box also having a top, a first side and a second side;
    b) a first storage cavity formed therein;
    c) a pair of formed slots for holding IV tubes, formed in said carrier box being placed adjacent to said first storage cavity; and
    d) a conical cavity, formed in said carrier box and being positioned adjacent to said pair of formed slots.

2. The equipment carrier of claim 1 further comprising a cavity formed in said carrier box for holding Keofeed tubing.

3. The equipment carrier of claim 1 further comprising a pair of slots for holding nasogastric suction tubing.

4. The equipment carrier of claim 1 further comprising a hook installed on the top of said carrier box.

5. The equipment carrier of claim 1 further comprising a strap, fixedly attached to the first side of said carrier box.

6. The equipment carrier of claim 1 further comprising a ring, fixedly attached to the first side of said carrier box.

7. The equipment carrier of claim 1 further comprising:
    a) a storage pouch; and
    b) a means for removably attaching said storage pouch from said second side of said carrier box.

8. The equipment carrier of claim 1 wherein the means for removably attaching said storage pouch from said second side of said carrier box comprises
    a) two straps, fixedly attached to said storage pouch and;
    b) a means for removably attaching said two straps to said carrier box.

9. The equipment carrier of claim 8 wherein the two straps and the means for removably attaching said storage pouch from said second side of said carrier box comprises a hook and loop type fastener.

10. The equipment carrier of claim 7 wherein said storage pouch has two pockets formed therein.

11. The equipment carrier of claim 7 wherein said storage pouch has one pocket formed therein.

12. The equipment carrier of claim 1 further comprising a storage pouch fixedly attached to a side of said housing.

13. The equipment carrier of claim 12 wherein said storage pouch has two pockets formed therein.

14. The equipment carrier of claim 12 wherein said storage pouch has one pocket formed therein.

* * * * *